(12) United States Patent
Kawano

(10) Patent No.: US 8,863,584 B2
(45) Date of Patent: Oct. 21, 2014

(54) MATERIAL TESTING SYSTEM

(75) Inventor: Toshiyuki Kawano, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 261 days.

(21) Appl. No.: 13/639,166

(22) PCT Filed: Jul. 22, 2010

(86) PCT No.: PCT/JP2010/062313
§ 371 (c)(1),
(2), (4) Date: Oct. 3, 2012

(87) PCT Pub. No.: WO2012/011173
PCT Pub. Date: Jan. 26, 2012

(65) Prior Publication Data
US 2013/0055823 A1 Mar. 7, 2013

(51) Int. Cl.
*G01N 3/00* (2006.01)
*G01N 3/08* (2006.01)

(52) U.S. Cl.
CPC .......... *G01N 3/08* (2013.01); *G01N 2203/0094* (2013.01); *G01N 2203/0208* (2013.01); *G01N 2203/0682* (2013.01)
USPC .............................................. 73/805; 73/788

(58) Field of Classification Search
CPC .............. G01N 3/00; G01N 3/08; G01L 1/10; G01B 7/02
USPC ........................................... 73/804, 805, 788
See application file for complete search history.

(56) References Cited

U.S. PATENT DOCUMENTS 3,774,237 A * 11/1973 Hardway, Jr. ................. 324/663
4,112,746 A * 9/1978 Itoh et al. ......................... 73/789
4,719,804 A * 1/1988 Maruyama ..................... 73/794

(Continued)

FOREIGN PATENT DOCUMENTS

CN 101339107 A 1/2009
JP 2001-033368 A 2/2001

(Continued)

OTHER PUBLICATIONS

International Search Report for PCT/JP2010/062313, mailing date of Aug. 31, 2010.

*Primary Examiner* — Max Noori
(74) *Attorney, Agent, or Firm* — Westerman, Hattori, Daniels & Adrian, LLP

(57) ABSTRACT

Provided is a material testing system that can prevent the influence of noise to obtain an adequate test result by reducing a variation in test force in a plastic region.
The material testing system is provided with: a displacement meter 15 that measures a displacement in distance between gage marks on a test piece 10; measuring means adapted to measure a displacement in rotational angle of a servo motor 31 that moves a crosshead 13; a computing part 48 that successively computes a change ratio R that is a ratio between the displacement in distance and the displacement in rotational angle; and a feedback control part 49 that, on the basis of the change ration R, performs feedback control of the servo motor 31, wherein when the change ratio R exceeds a setting value, a value of a parameter K used for the feedback control is changed to a value that makes the influence of the feedback control small.

8 Claims, 3 Drawing Sheets

(56) References Cited

U.S. PATENT DOCUMENTS

| | | | |
|---|---|---|---|
| 5,691,473 A * | 11/1997 | Peleg | 73/573 |
| 7,770,467 B1 * | 8/2010 | Halderman et al. | 73/856 |
| 8,006,568 B2 * | 8/2011 | Halderman et al. | 73/856 |
| 2009/0007689 A1 | 1/2009 | Kawano | |
| 2010/0251838 A1 * | 10/2010 | Halderman et al. | 73/866.5 |
| 2013/0312534 A1 * | 11/2013 | Li et al. | 73/774 |

FOREIGN PATENT DOCUMENTS

| | | |
|---|---|---|
| JP | 2002-365188 A | 12/2002 |
| JP | 2005-337812 A | 12/2005 |
| JP | 2009-014499 A | 1/2009 |
| JP | 2010-048740 A | 3/2010 |
| JP | 2010-48740 A | 3/2010 |

\* cited by examiner

MATERIAL TESTING SYSTEM

TECHNICAL FIELD

The present invention relates to a material testing system, and in particular, to a material testing system that performs testing on a test piece having an elastic region and a plastic region.

BACKGROUND ART

Such a material testing system has a configuration in which, for example, a pair of screw rods is supported on a table rotatably in synchronization with each other, and both end parts of a crosshead are supported by the screw rods through nuts. Also, by using rotation of a motor to rotate the pair of screw rods in synchronization with each other, the crosshead is moved along the pair of screw rods. The crosshead and the table are respectively connected with grippers. The material testing system is configured to, in a state where both ends of a test piece are gripped by the pair of grippers, move the crosshead to thereby apply a load to the test piece.

In such a material testing system, as the motor for rotating the screw rods, a servomotor is typically used. For example, as described in JPA 2002-365188 as Patent literature 1, among test force acting on a test piece, elongation of the test piece, and the like, a transient detection value of a physical quantity selected as a control variable is set as a target value to perform feedback, and thereby a motor is controlled. That is, in the case where the test force is selected as the control variable, a calculation such as PID is performed on a deviation between a detection value (current value) of the test force and the target value, and a value corresponding to a result of the calculation is given as a rotational angular speed command to a servo amplifier, which supplies a driving signal to the driving motor, to thereby control the motor. More specifically, a value obtained by multiplying the deviation by a constant (proportional gain), a value obtained by multiplying time derivative of the deviation by a constant (derivative gains), and a value obtained by multiplying time integration by a constant (integral gain) are combined to determine the magnitude of the rotational angular speed command.

In a material testing system using such a motor as a driving source, unless the above-described proportional gain, derivative gain, and integral gain are adequately set, accurate material testing that correctly follows a target value cannot be performed. However, the real situation is that the gains are set by trial and error. For this reason, there are problems that, in particular, when material testing is performed on a new type of a test piece, it takes long time to set the gains, and also an operator should be skillful.

JPA 2009-14499 as Patent literature 2 discloses a material testing system that uses a motor as a driving source of a loading mechanism for applying a load to a test piece, and is provided with a control mechanism that successively gives a rotational angular speed command for the motor to a servo amplifier driving the motor and thereby controls operation of the load mechanism. In the material testing system, test force that serves as a control variable and acts on the test piece, or test piece elongation as a control variable is first detected as a detection value. Then, according to a deviation between the detection value and a target value, the magnitude of a rotational angular speed, which is to be supplied to the servo amplifier as the command, is computed. After that, a ratio of the detection value of the control variable to a displacement of the motor is successively computed, and a value proportional to a value obtained by dividing the deviation by the computed ratio is set as the magnitude of the rotational angular speed, which is to be supplied to the servo amplifier as the command.

According to the material testing system described in JPA 2009-14499, without requiring skill for setting of control gain, or doing trial-and-error work for the setting for a long time, accurate material testing can be constantly performed.

CONVENTIONAL TECHNIQUE LITERATURE

Patent literature

[Patent literature 1] JPA No. 2002-365188
[Patent literature 2] JPA No. 2009-14499

SUMMARY OF THE INVENTION

Problem to be Solved by the Invention

In the case of performing tensile testing on a test piece having an elastic region and a plastic region, such as a steel material, in the elastic region, a ratio of a displacement between gage marks on the test piece to a movement of a crosshead for moving one of grippers is approximately 10% to 50%. That is, when tensile force is loaded on the test piece, due to deformation of the whole of a load mechanism such as grippers that grip the test piece, and the crosshead for moving the gripper, deformation of a region other than a region between the gage marks on the test piece, or the like, the ratio of the displacement between the gage marks on the test piece becomes small as compared with the movement of the crosshead.

On the other hand, in the plastic region, local deformation occurs in the region between the gage marks on the test piece, whereas in the region other than the region between the gage marks, deformation hardly occurs, and therefore the ratio of the displacement between the gage marks on the test piece to the movement of the crosshead takes a value close to approximately 1.

Note that, in a typical elastic region, test force (tensile force) acting on a test piece increases in proportion to a movement of a crosshead, whereas in a plastic region, a large variation does not occur in the test force. On the other hand, the test force highly depends on moving speed of the crosshead, and if the moving speed of the crosshead is changed during testing, a variation in test force due to the change in test speed occurs accordingly.

As described in above Patent literature 2, in the material testing system provided with the control mechanism that gives the rotational angular speed command for the motor to the servo amplifier driving the motor and thereby controls the operation of the load mechanism, such a phenomenon where the test speed is changed along with the control operation occurs.

If a variation in test force along with such a change in test speed occurs particularly in a plastic region, the following problem occurs. That is, if the test speed is changed, the variation in test force occurs; however, in the plastic region, the test force during testing takes an almost constant value, and the variation is small, so that the variation in test force due to a minute change in test speed relatively largely occurs, and therefore when a result of the testing is graphed, a smooth graph is not created but a graph including noise is created.

The present invention is made in order to solve the above-described problem, and intended to provide a material testing system that can prevent the influence of noise to obtain an adequate test result by reducing a variation in test force in a plastic region.

Means Adapted to Solve the Problem

An invention according to a first aspect of the present invention is a material testing system that performs testing on a test piece having an elastic region and a plastic region, and the material testing system is provided with: a pair of grippers that grips both ends of the test piece; a moving member that moves one gripper of the pair of grippers; a displacement meter that measures a displacement in a distance between gage marks on the test piece at the time when the one gripper is moved by the moving member; movement measuring means adapted to measure a movement of the moving member; computing means adapted to successively compute a change ratio R that is a ratio between the displacement in the distance, the displacement being measured by the displacement meter, and the movement of the moving member, the movement being measured by the movement measuring means; means adapted to, on the basis of the successively computed change ratio R, compute a parameter used to perform feedback control of the movement of the moving member; and a feedback control part, wherein when the change ratio R exceeds a setting value, the feedback control part changes a value of the parameter K used for the feedback control to a value that makes an influence of the feedback control small, and performs the feedback control.

An invention according to a second aspect of the present invention is the invention according to the first aspect, wherein when the change ratio R exceeds the setting value, the feedback control part fixes the value of the parameter K used for the feedback control to a predetermined value to perform the feedback control.

An invention according to a third aspect of the present invention is the invention according to the second aspect, wherein when the change ratio R exceeds the setting value, the feedback control part fixes the value of the parameter K used for the feedback control to a value between a value of R at the time of the excess and 1 to perform the feedback control.

An invention according to a fourth aspect of the present invention is the invention according to the second aspect, wherein when the change ratio R exceeds the setting value, the feedback control part fixes the value of the parameter K used for the feedback control to a value of R at the time of the excess to perform the feedback control.

An invention according to a fifth aspect of the present invention is the invention according to the first aspect, wherein when the change ratio R exceeds the setting value, the feedback control part performs a calculation process on the value of the parameter K used for the feedback control so as to bring a variation ratio of the value of K to a small value, and performs the feedback control.

An invention according to a sixth aspect of the present invention is the invention according to any of the first to fifth aspects, wherein the setting value is 0.7.

An invention according to a seventh aspect of the present invention is the invention according to the sixth aspect, wherein: a moving mechanism that moves the moving member is provided with a motor used to move the moving member and a servo amplifier driving the motor; and the movement measuring means measures the movement on the basis of a displacement in a rotational angle of the motor.

An invention according to an eighth aspect of the present invention is the invention according to the seventh aspect, wherein a value obtained by multiplying, by a reciprocal of a preset time constant, a value obtained by dividing a deviation between a target value of the displacement in the distance and a detection value of the displacement in the distance by the parameter K is set as magnitude of the rotational angle, the magnitude being to be supplied to the servo amplifier.

Effects of the Invention

According to the inventions according to the first to sixth aspects, on the basis of the successively computed change ratio R, the feedback control is performed, and therefore adequate material testing can be constantly performed. At this time, by reducing a variation in test force in the plastic region, the influence of noise can be prevented to obtain an adequate test result.

According to the inventions according to the seventh and eighth aspects, in the material testing system using the motor as a driving source, it is not necessary to set gain for performing the feedback control of the motor, and therefore without requiring skill for setting of the gain, or doing trial-and-error work for the setting for a long time, accurate material testing can be constantly performed.

EMBODIMENTS OF THE INVENTION

Figure 1:
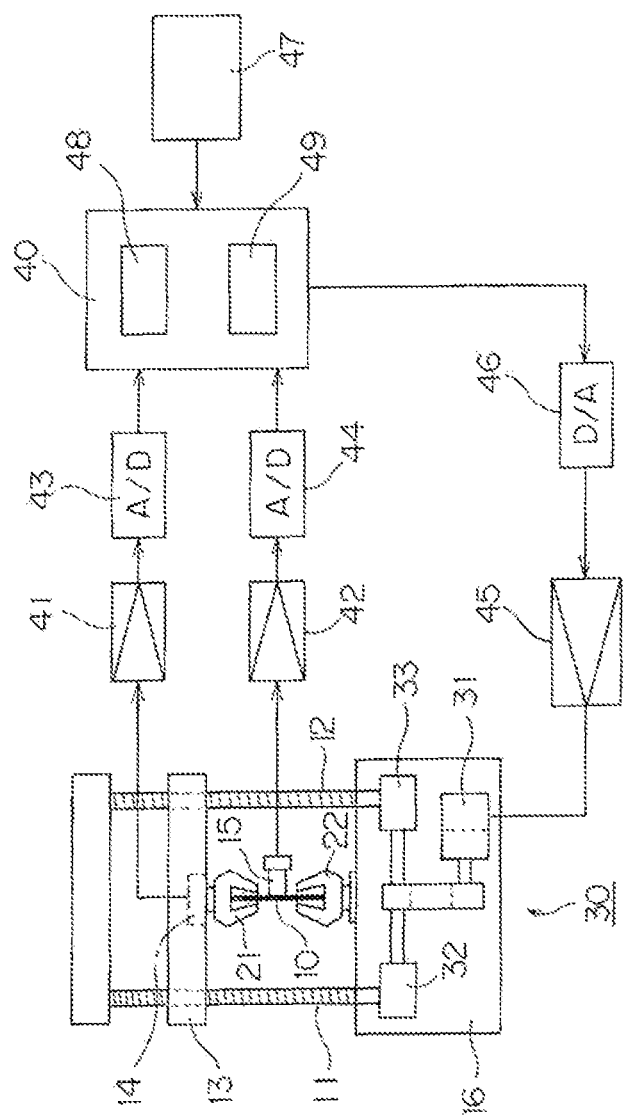
FIG. 1 is an outline diagram of a material testing system according to the present invention.
Figure 2:
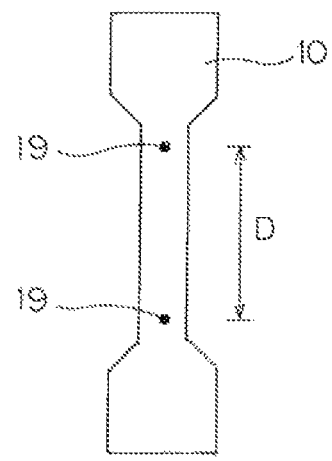
FIG. 2 is an outline diagram of a test piece 10.

Embodiments of the present invention will hereinafter be described on the basis of the drawings. FIG. 1 is an outline diagram of a material testing system according to the present invention. In the outline diagram, a schematic diagram representing a mechanical configuration and a block diagram representing an electrical configuration are illustrated together. Also, FIG. 2 is an outline diagram of a test piece 10.

The material testing system is provided with: a table 16; a pair of screw rods 11 and 12 that is rotatably provided upright on the table 16 with facing in a vertical direction; a crosshead 13 that is movable along the screw rods 11 and 12; and a load mechanism 30 that is intended to move the crosshead 13 to apply a load to the test piece 10.

The crosshead 13 is connected to the pair of screw rods 11 and 12 through unillustrated nuts. Lower end parts of the respective screw rods 11 and 12 are connected with worm reducers 32 and 33 in the load mechanism 30, respectively. The material testing system is configured such that the worm reducers 32 and 33 are connected to a servo motor 31 that is a driving source of the load mechanism 30, and rotation of the servo motor 31 is transmitted to the pair of screw rods 11 and 12 through the worm reducers 32 and 33, respectively. The rotation of the servo motor 31 causes the pair of screw rods 11 and 12 to rotate in synchronization with each other, and thereby the crosshead 13 moves up and down along the screw rods 11 and 12.

On the crosshead 13, an upper gripper 21 for gripping an upper end part of the test piece 10 is annexed. The crosshead 13 functions as a moving member according to the present invention. On the other hand, on the table 16, a lower gripper 22 for gripping a lower end part of the test piece 10 is annexed. In the case of performing tensile testing, by moving up the crosshead 13 with gripping both of the end parts of the test piece 10 by the upper and lower grippers 21 and 22, test force (tensile load) F is loaded on the test piece 10.

At this time, the test force acting on the test piece 10 is detected by a load cell 14; amplified by a load amplifier 41; then digitalized by an AD converter 43; and inputted to a calculation control part 40. Also, a displacement in distance D (see FIG. 2) between gage marks 19 on the test piece 10 is measured by a displacement meter 15; amplified by a strain amplifier 42; then digitalized by an AD converter 44; and inputted to the calculation control part 40.

The calculation control part 40 is configured to include a computer and a sequencer, and peripheral devices of them, and takes in test force data and displacement data from the load cell 14 and the displacement meter 15, respectively, to perform data processing. Also, the servo motor 31 is rotationally driven by current supplied from a servo amplifier 45. The servo amplifier 45 supplies to the servo motor 31 the current depending on the magnitude of a rotational angular speed command supplied from the calculation control part 40 through a D/A converter 46. The servo motor 31 is feedback controlled by the calculation control part 40. At this time, the calculation control part 40 also functions as movement measuring means adapted to, on the basis of a displacement in rotational angle of the servo motor 31, measure a movement of the crosshead 13.

The calculation control part 40 includes: a computing part 48 for successively computing an after-mentioned change ratio R; and a feedback control part 49 for, on the basis of the computed change ratio R, determining a parameter K necessary to perform the feedback control, and performing the feedback control. Also, the calculation control part 40 is connected with an operation part 47, and can give various types of commands and set a constant A corresponding to an after-mentioned time constant on the basis of operation of the operation part 47.

At this time, calculation expressions described below are used. That is, in the material testing system according to the present invention, given that the displacement in rotational angle of the servo motor 31 is θ(t), and a detection value (current value) of the displacement (elongation) in distance D between the gage marks 19 on the test piece 10 is E(t), the change ratio R(t) expressed by following Expression (1) using the displacement θ(t−t0) in rotational angle of the servo motor 31 at time (t−t0) that is a certain time before t, and the displacement E(t−t0) in distance D between the gage marks is successively computed:

[Expression 1]

$$R(t) = \frac{E(t) - E(t-t0)}{\theta(t) - \theta(t-t0)} \quad (1)$$

As a method for calculating K from R,
[Expression 2]

$$R(t) = K(t) \quad (2)$$

may be set; however,
[Expression 3]

$$K(t) = K(t-t0) + (R(t) - K(t-t0)) \times a \quad (3)$$

(where a is a coefficient and meets 0<a<1)
can also be set.

In this case, given that a=1, Expression (2) holds, and as a is brought close to 0, a change in K becomes small.

Also, a value proportional to a value obtained by dividing a deviation by the parameter K(t) obtained by Expression (3) is set as the magnitude of rotational angular speed dθ/dt to be supplied to the servo amplifier 45. If this is expressed by an expression, given that the current detection value of the displacement in distance D between the gage marks 19, which is the control variable, is E(t), the target value of the control variable at the time of the detection is Ed(t), and the deviation is {Ed(t)−E(t)}, the rotational angular speed dθ/dt to be supplied to the servo amplifier 45 is expressed by following Expression (4):

[Expression 4]

$$\frac{d\theta(t)}{dt} = \frac{A}{K(t)} \{Ed(t) - E(t)\} \quad (4)$$

Here, in Expression (4), A is a preset constant, which corresponds to a reciprocal of a time constant (time constant of a change in deviation) in the invention according to claim 7. If fast convergence of the deviation is desired, it is only necessary to set A large, whereas if slow convergence is acceptable, it is only necessary to set A small.

According to the present invention, a ratio to the deviation of the magnitude dθ/dt of the transient rotational angular speed command supplied to the servo amplifier 45 for the driving servo motor 31 of the load mechanism 30 is automatically determined depending on a ratio of a change in detection value of the displacement in distance D between the gage marks 19 to the displacement in rotational angle of the servo motor 31, and controlled to be small if the ratio of the change is in a large state, and to become large if the ratio of the change becomes small. In other words, in the case where the ratio of the change is large, proportional gain is automatically set small, whereas in the case where the ratio of the change becomes small, the proportional gain is automatically set large. This enables accurate material testing to be constantly performed without setting the gain by trial and error prior to the testing.

The present invention is based on the assumption that a relationship between the displacement in distance D between the gage marks 19, which is the control variable, and the rotational angle of the servo motor 31 is transiently a proportional relationship, and a constant of the proportionality changes due to plastic deformation of the test piece associated with progress of the testing. That is, given that the displacement of the servo motor 31 from the beginning of the testing is θ(t), and the detection value of the displacement in distance D between the gage marks 19, which is selected as the control variable, is E(t), following Expression (5) holds:
[Expression 5]

$$E(t) - Er(t) = K(t) \times \theta(t) \quad (5)$$

That is, Expression (5) indicates that the displacement E(t) in distance D between the gage marks 19, which is the control variable, is proportional to the displacement θ(t) in rotational angle of the servo motor 31, and Er(t) changes with time, and therefore both of them does not have a proportional relation ship in a precise sense. Here, in Expression (5), a term other than a proportional term is expressed by Er(t).

Figure 3:
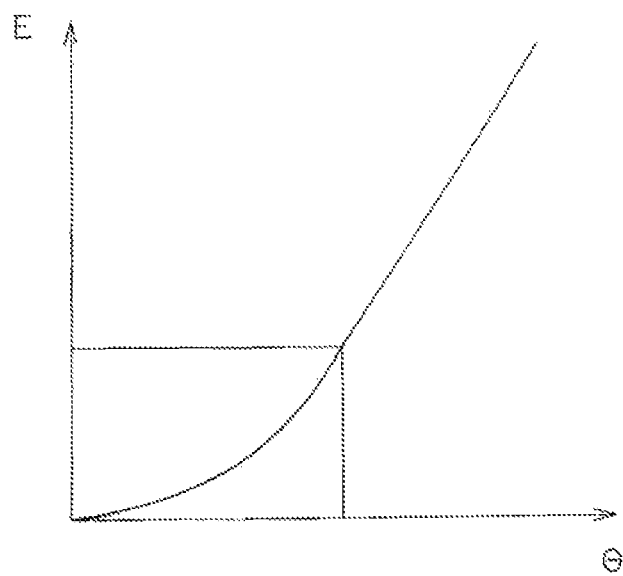
FIG. 3 is a graph illustrating a relationship between a displacement E(t) in distance D between gage marks 19 and a displacement θ(t) in rotational angle of a servo motor 31.

FIG. 3 is a graph illustrating a relationship between the displacement E(t) in distance D between the gage marks 19 and the displacement θ(t) in rotational angle of the servo motor 31. In the graph of FIG. 3, the horizontal axis represents the displacement θ(in the case where at the beginning of the testing, the rotational angle is set to 0) in rotational angle of the motor, and the vertical axis represents the detection value of the displacement E in distance D between the gage marks 19 as the control variable. Differentiating both sides of Expression (5) with respect to time results in Expression (6).

[Expression 6]

$$\frac{dE(t)}{dt} - \frac{dEr(t)}{dt} = K(t)\frac{d\theta(t)}{dt} + \frac{dK(t)}{dt}\theta(t) \quad (6)$$

In general, dEr(t)/dt does not become 0, but serves as a parameter that changes with time due to a change in property of the test piece 10 associated with the progress of the testing; however, the change in material property is typically a relatively slow change, and the time change dEr(t)/dt takes a sufficiently small value and can be therefore handled as dEr(t)/dt=0. Similarly, K(t) also changes with time; however, on the assumption that the change is small, given that dK(t)/dt=0, following Expression (7) holds:

[Expression 7]

$$\frac{dE(t)}{dt} = K(t) \times \frac{d\theta(t)}{dt}. \quad (7)$$

Here, in the case of, as control input, i.e., as an operation variable for the servo amplifier 45, using the rotational angular speed dθ/dt of the servo motor 31, the actual rotational angular speed dθ/dt of the servo motor 31 depends on a load on the servo motor 31, and does not have a value completely equal to the magnitude dθ/dt of the rotational angular speed command supplied to the servo amplifier 45; however, in the case of using the typical servo motor 31 and servo amplifier 45, the both have values sufficiently close to each other. For this reason, Expression (7) can be approximated as follows:

[Expression 8]

$$\frac{dE(t)}{dt} = K(t) \times \frac{d\theta}{dt}. \quad (8)$$

Also, K(t) changes in association with the progress of the testing, so that the transient detection value of the displacement E(t) in distance D between the gage marks 19, which is the control variable, and the displacement in rotational angle of the servo motor 31 are used to successively compute K(t), and the computed K(t) and a deviation at the time are used to compute the magnitude of the rotational angular speed command for the servo motor 31, which is to be supplied to the servo amplifier 43, by above-described Expression (4).

Substituting Expression (4) into Expression (7) results in following Expression (9):

[Expression 9]

$$\frac{dE(t)}{dt} = A\{Ed(t) - E(t)\}. \quad (9)$$

Then, by defining following Expression (10), Expression (11) holds.

[Expression 10]

$$G = E(t) - Ed(t) \quad (10)$$

[Expression 11]

$$\frac{dE(t)}{dt} = -AG \quad (11)$$

Here, A represents the time constant of a change in deviation. Accordingly, it is only necessary to, in consideration of a desired time constant, make a determination. For example, in the case of A=1, regarding the time change in deviation with respect to a step response, given that the time derivative dE0/dt of a target value of the step response is zero, following Expression (12) holds, and the deviation after 1 second can be computed as exp(−1)=0.36.

[Expression 12]

$$G = \exp(-t) \quad (12)$$

In the case of employing the above configuration, in the material testing system using the servo motor 31 as the driving source of the load mechanism 30, it is not necessary to set gain for performing the feedback control of the servo motor 31, and from the transient displacement in rotational angle of the servo motor 31 and detection value of the control variable, transient adequate gain is automatically computed and successively set. Accordingly, an operator is not required to make the gain setting by trial and error prior to the testing as in the conventional case, and simultaneously with being able to omit time and effort for the setting, can constantly perform accurate material testing without requiring any skill.

As described above, in the material testing system according to the present invention, the rotational angular speed dθ/dt to be supplied to the servo amplifier 45 is controlled to meet above-described Expression (4). That is, if a value of the change ratio R expressed by Expression (1) is computed, and on the basis of this, K is computed and changed by Expression (2) or (3), the rotational angular speed dθ/dt to be supplied to the servo amplifier 45 is changed, and moving speed of the crosshead 13 is changed. Note that the test force highly depends on the moving speed of the crosshead 13, and if during the testing, the moving speed of the crosshead 13 is changed, a variation in test force due to the change in test speed occurs accordingly. If the variation in test force associated with the change in test speed occurs particularly in a plastic region, because in the plastic region, local deformation occurs in a region between the gage marks on the test piece, and large deformation occurs by small test force, a minute change in speed causes the test force to be varied, and noise associated with the variation in test force directly leads to a variation in deformation. For this reason, when a result of the testing is graphed, a smooth graph cannot be created, but a graph including the above-described noise is created.

Therefore, in the material testing system according to the present invention, the computing part 48 in the calculation control part 40 successively computes the change ratio R, and constantly monitors whether the change ratio R exceeds a setting value of 0.7 that is preset.

As described above, in the case of performing the tensile testing on the test piece having an elastic region and a plastic region, such as a steel material, in the elastic region, a ratio of the displacement between the gage marks 19 on the test piece 10 to the movement of the crosshead 13 is approximately 10% to 50%. On the other hand, in the plastic region, in the region between the gage marks on the test piece 10, local deformation occurs, and in the other region, deformation hardly occurs. For this reason, the ratio of the displacement between the gage marks 19 on the test piece 10 to the movement of the crosshead 13 is close to 1. Accordingly, on the basis of whether the above-described value of the change ratio R exceeds, for example, 0.7, it can be determined whether a region of the test piece 10 currently under testing is the elastic region or the plastic region.

If the change ratio R exceeds 0.7, it is determined that the region of the test piece 10 is the plastic region; then a value of the parameter K is changed to a value that makes the influence of the feedback control small; and the changed parameter K is used to perform subsequent feedback control.

That is, in one embodiment, at the point when the change ratio R exceeds the setting value of 0.7, a value of the parameter K, which is used for the feedback control, is fixed to a predetermined value to perform the feedback control. The value of K at this time is fixed to a value between the value at that time and 1 to perform the feedback control. Alternatively, the value of K at this time is fixed to the value at that time to perform the feedback control.

As described, when the change ratio R exceeds the setting value, a value of K is fixed to a value that makes the influence of the feedback control small, and the feedback control is performed, so that a variation in test force can be reduced in the plastic region. For this reason, the influence of noise associated with the variation in test force can be prevented, and when a result of the testing is graphed, a smooth graph can be created.

Also, in another embodiment, at the point when the change ration R exceeds 0.7, a calculation process that brings a variation ratio of a value of the parameter K, which corresponds to a value of the change ratio R and is used for the feedback control, to a small value is performed to perform the feedback control. More specifically, when the change ratio R exceeds 0.7, the computing part 48 in the calculation control part 40 performs a calculation that decreases the variation ratio of the value of the K under a certain condition, and also the feedback control part 49 performs the feedback control with use of K taking into account the calculated variation ratio. Even in this case, the influence of noise associated with the variation in test force can be prevented, and when a result of the testing is graphed, a smooth graph can be created.

Note that a value of the above-described setting value is not limited to 0.7, but is only required to be appropriately set depending on a relationship between the material testing system and the test piece 10. For example, in the case where the material testing system is sufficiently large-sized, and has sufficient rigidity relative to the test piece 10, it is only necessary to set a value larger than 0.7 and close to 1 as the setting value, whereas in the case where the rigidity of the material testing system is small, it is only necessary to set a value smaller than 0.7 as the setting value. Also, for example, the present invention may be configured such that the ratio of the displacement between the gage marks 19 on the test piece 10 to the movement of the crosshead 13 in the elastic region is preliminarily measured, and the setting value is set with being related to the ratio.

Explanations of Letters or Numerals

10: Test piece
11: Screw rod
12: Screw rod
13: Crosshead
14: Load cell
15: Displacement meter
16: Table
21: Upper gripper
22: Lower gripper
30: Load mechanism
31: Servo motor
32: Worm reducer
33: Worm reducer
40: Calculation control part
41: Load amplifier
42: Strain amplifier
45: Servo amplifier
47: Operation part
48: Computing part
49: Feedback control part

What is claimed is:

1. A material testing system that performs testing on a test piece having an elastic region and a plastic region, the material testing system comprising:
   a pair of grippers that grips both ends of the test piece;
   a moving member that moves one gripper of the pair of grippers;
   a displacement meter that measures a displacement in a distance between gage marks on the test piece at a time when the one gripper is moved by the moving member;
   movement measuring means adapted to measure a movement of the moving member;
   computing means adapted to successively compute a change ratio R that is a ratio between the displacement in the distance, the displacement being measured by the displacement meter, and the movement of the moving member, the movement being measured by the movement measuring means;
   means adapted to, on a basis of the successively computed change ratio R, compute a parameter K used to perform feedback control of the movement of the moving member; and
   a feedback control part, wherein
   when the change ratio R exceeds a setting value, the feedback control part changes a value of the parameter K used for the feedback control to a value that makes an influence of the feedback control small, and performs the feedback control.

2. The material testing system according to claim 1, wherein
   when the change ratio R exceeds the setting value, the feedback control part fixes the value of the parameter K used for the feedback control to a predetermined value to perform the feedback control.

3. The material testing system according to claim 2, wherein
   when the change ratio R exceeds the setting value, the feedback control part fixes the value of the parameter K used for the feedback control to a value between a value of R at a time of the excess and 1 to perform the feedback control.

4. The material testing system according to claim 2, wherein
   when the change ratio R exceeds the setting value, the feedback control part fixes the value of the parameter K used for the feedback control to a value of R at a time of the excess to perform the feedback control.

5. The material testing system according to claim 1, wherein
   when the change ratio R exceeds the setting value, the feedback control part performs a calculation process on the value of the parameter K used for the feedback control so as to bring a variation ratio of the value of K to a small value, and performs the feedback control.

6. The material testing system according to any of claims 1 to 5, wherein
   the setting value is 0.7.

7. The material testing system according to claim 6, wherein:
- a moving mechanism that moves the moving member is provided with a motor used to move the moving member and a servo amplifier driving the motor; and
- the movement measuring means measures the movement on a basis of a displacement in a rotational angle of the motor.

8. The material testing system according to claim 7, wherein
- a value obtained by multiplying, by a reciprocal of a preset time constant, a value obtained by dividing a deviation between a target value of the displacement in the distance and a detection value of the displacement in the distance by the parameter K is set as magnitude of the rotational angle, the magnitude being to be supplied to the servo amplifier.

* * * * *